(12) United States Patent
Boyd et al.

(10) Patent No.: US 7,151,191 B2
(45) Date of Patent: Dec. 19, 2006

(54) COMPOUNDS AND COMPOSITIONS FOR DELIVERING ACTIVE AGENTS

(75) Inventors: Maria Aurora P. Boyd, Garrison, NY (US); Andrea Leone-Bay, Ridgefield, CT (US); Doris C. O'Toole, Carmel, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 194 days.

(21) Appl. No.: 10/181,275

(22) PCT Filed: Jan. 12, 2001

(86) PCT No.: PCT/US01/01274

§ 371 (c)(1),
(2), (4) Date: Aug. 5, 2002

(87) PCT Pub. No.: WO01/51454

PCT Pub. Date: Jul. 19, 2001

(65) Prior Publication Data

US 2003/0149296 A1    Aug. 7, 2003

Related U.S. Application Data

(60) Provisional application No. 60/202,210, filed on May 5, 2000, provisional application No. 60/194,421, filed on Apr. 4, 2000, provisional application No. 60/175,947, filed on Jan. 13, 2000.

(51) Int. Cl.
  *C07C 229/00* (2006.01)
  *C07C 233/00* (2006.01)
  *A01N 37/18* (2006.01)

(52) U.S. Cl. .......................... 562/455; 554/47; 514/620

(58) Field of Classification Search ................ 514/620; 562/455; 554/47
See application file for complete search history.

(56) References Cited

U.S. PATENT DOCUMENTS

| | | | |
|---|---|---|---|
| 3,398,187 A | 8/1968 | Drain | |
| 3,781,328 A * | 12/1973 | Witte | 560/42 |
| 4,032,635 A * | 6/1977 | Umezawa et al. | 514/166 |
| 4,072,753 A * | 2/1978 | Umezawa et al. | 514/533 |
| 4,238,506 A | 12/1980 | Stach et al. | |
| 4,442,090 A | 4/1984 | Kakeya et al. | |
| 4,462,991 A | 7/1984 | Higuchi et al. | |
| 4,757,066 A | 7/1988 | Shiokari et al. | |
| 4,835,312 A | 5/1989 | Itoh et al. | |
| 4,873,087 A | 10/1989 | Morishita et al. | |
| 4,900,730 A | 2/1990 | Miyauchi | |
| 4,927,928 A | 5/1990 | Shroot et al. | |
| 5,122,539 A | 6/1992 | Abraham et al. | 514/563 |
| 5,304,575 A | 4/1994 | Beck | 514/563 |
| 5,443,841 A | 8/1995 | Milstein et al. | |
| 5,447,728 A | 9/1995 | Milstein et al. | |
| 5,451,410 A | 9/1995 | Milstein et al. | |
| 5,541,155 A | 7/1996 | Leone-Bay et al. | |
| 5,629,020 A | 5/1997 | Leone-Bay et al. | |
| 5,643,957 A | 7/1997 | Leone-Bay et al. | |
| 5,650,386 A | 7/1997 | Leone-Bay et al. | |
| 5,709,861 A | 1/1998 | Santiago et al. | |
| 5,714,167 A | 2/1998 | Milstein et al. | |
| 5,766,633 A | 6/1998 | Milstein et al. | |
| 5,773,647 A | 6/1998 | Leone-Bay et al. | |
| 5,776,888 A | 7/1998 | Leone-Bay et al. | |
| 5,804,688 A | 9/1998 | Leone-Bay et al. | |
| 5,811,127 A | 9/1998 | Milstein et al. | |
| 5,863,944 A | 1/1999 | Leone-Bay et al. | |
| 5,866,536 A | 2/1999 | Leone-Bay et al. | |
| 5,876,710 A | 3/1999 | Leone-Bay et al. | |
| 5,879,681 A | 3/1999 | Leone-Bay et al. | |
| 5,935,601 A | 8/1999 | Leone-Bay et al. | |
| 5,939,381 A | 8/1999 | Leone-Bay et al. | |
| 5,955,503 A | 9/1999 | Leone-Bay et al. | |
| 5,958,457 A | 9/1999 | Santiago et al. | |
| 5,962,710 A | 10/1999 | Gschneidner et al. | |
| 5,965,121 A | 10/1999 | Leone-Bay et al. | |
| 5,989,539 A | 11/1999 | Leone-Bay et al. | |
| 5,990,166 A | 11/1999 | Leone-Bay et al. | |
| 6,001,347 A | 12/1999 | Leone-Bay et al. | |
| 6,051,561 A | 4/2000 | Leone-Bay et al. | |
| 6,060,513 A | 5/2000 | Leone-Bay et al. | |
| 6,071,510 A | 6/2000 | Leone-Bay et al. | |
| 6,071,538 A | 6/2000 | Milstein et al. | |
| 6,084,112 A | 7/2000 | Ho et al. | |
| 6,090,958 A | 7/2000 | Leone-Bay et al. | |
| 6,099,856 A | 8/2000 | Milstein et al. | |
| 6,100,298 A | 8/2000 | Leone-Bay et al. | |
| 6,180,140 B1 | 1/2001 | Leone-Bay et al. | |
| 6,221,367 B1 | 4/2001 | Milstein et al. | |
| 6,242,495 B1 | 6/2001 | Leone-Bay et al. | |
| 6,245,359 B1 | 6/2001 | Milstein et al. | |
| 6,313,088 B1 | 11/2001 | Leone-Bay et al. | |

(Continued)

FOREIGN PATENT DOCUMENTS

EP     0 036 145 A1    9/1981

(Continued)

OTHER PUBLICATIONS

Goa et al, Drug, 52(5) pages 725 to 752 (1996).*

(Continued)

*Primary Examiner*—Samuel Barts
*Assistant Examiner*—Kellette Gale
(74) *Attorney, Agent, or Firm*—Darby & Darby

(57) ABSTRACT

Compounds and compositions for the delivery of active agents are provided. Methods of administration and preparation are provided as well.

37 Claims, No Drawings

U.S. PATENT DOCUMENTS

| | | |
|---|---|---|
| 6,344,213 B1 | 2/2002 | Leone-Bay et al. |
| 6,346,242 B1 | 2/2002 | Leone-Bay et al. |
| 6,348,207 B1 | 2/2002 | Milstein et al. |
| 6,358,504 B1 | 3/2002 | Leone-Bay et al. |
| 6,384,278 B1 | 5/2002 | Tang et al. |
| 6,391,303 B1 | 5/2002 | Haas et al. |
| 6,399,798 B1 | 6/2002 | Gschneidner et al. |
| 6,428,780 B1 | 8/2002 | Leone-Bay et al. |
| 6,440,929 B1 | 8/2002 | Milstein et al. |
| 6,461,643 B1 | 10/2002 | Milstein et al. |
| 6,525,020 B1 | 2/2003 | Leone-Bay et al. |
| 6,610,329 B1 | 8/2003 | Santiago et al. |
| 6,623,731 B1 | 9/2003 | Leone-Bay et al. |
| 6,627,228 B1 | 9/2003 | Milstein et al. |
| 6,642,411 B1 | 11/2003 | Leone-Bay et al. |
| 6,646,162 B1 | 11/2003 | Tang et al. |
| 6,663,887 B1 | 12/2003 | Leone-Bay et al. |
| 6,693,073 B1 | 2/2004 | Milstein et al. |
| 6,693,208 B1 | 2/2004 | Gscheidner et al. |
| 6,699,467 B1 | 3/2004 | Leone-Bay et al. |
| 2002/0001591 A1 | 1/2002 | Santiago et al. |

FOREIGN PATENT DOCUMENTS

| | | |
|---|---|---|
| EP | 0 576 941 A1 | 1/1994 |
| ES | 369853 A1 | 7/1969 |
| FR | 4446 A1 | 9/1966 |
| FR | 1 571 198 A | 6/1969 |
| GB | 1088295 * | 10/1967 |
| GB | 2 095 994 A1 | 10/1982 |
| JP | 57-171946 * | 10/1982 |
| JP | 2 239 980 A1 | 9/1990 |
| JP | 7-149045 * | 6/1995 |
| WO | WO 98/05331 | 2/1994 |
| WO | WO-95/28838 A1 | 11/1995 |
| WO | WO-95/28920 A1 | 11/1995 |
| WO | WO-96/12473 A1 | 5/1996 |
| WO | WO-96/12474 A1 | 5/1996 |
| WO | WO-96/12475 A1 | 5/1996 |
| WO | WO-96/21464 A1 | 7/1996 |
| WO | WO-96/30036 A | 10/1996 |
| WO | WO-97/10197 A1 | 3/1997 |
| WO | WO-97/36480 A1 | 10/1997 |
| WO | WO-97/47270 A1 | 12/1997 |
| WO | WO 98/05331 * | 2/1998 |
| WO | WO-98/21951 A1 | 5/1998 |
| WO | WO-98/25589 A1 | 6/1998 |
| WO | WO-98/34632 A1 | 8/1998 |
| WO | WO-98/50341 A1 | 11/1998 |
| WO | WO-99/16427 A1 | 4/1999 |
| WO | WO-99/29705 A1 | 6/1999 |
| WO | WO 98/40904 | 8/1999 |
| WO | WO-00/06184 A1 | 2/2000 |
| WO | WO-00/06534 A1 | 2/2000 |
| WO | WO-00/07979 A1 | 2/2000 |
| WO | WO-00/40203 A1 | 7/2000 |
| WO | WO-00/46182 A1 | 8/2000 |
| WO | WO-0050386 A1 | 8/2000 |
| WO | WO-00/59480 A1 | 10/2000 |
| WO | WO-00/59863 A1 | 10/2000 |
| WO | WO-01/32130 A1 | 5/2001 |
| WO | WO-01/32596 A1 | 5/2001 |
| WO | WO-01/44199 A1 | 6/2001 |
| WO | WO-01/51454 A1 | 7/2001 |
| WO | WO-01/70219 A1 | 9/2001 |
| WO | WO-01/92206 A1 | 12/2001 |
| WO | WO-02/02509 A1 | 1/2002 |
| WO | WO-02/15959 A1 | 2/2002 |
| WO | WO-02/16309 A1 | 2/2002 |
| WO | WO-02/19969 A1 | 3/2002 |
| WO | WO-02/20466 A1 | 3/2002 |
| WO | WO-02/069937 A1 | 9/2002 |
| WO | WO-02/070438 A1 | 9/2002 |
| WO | WO-02/100338 A1 | 12/2002 |
| WO | WO-03/026582 A1 | 4/2003 |
| WO | WO-03/045306 A1 | 6/2003 |
| WO | WO-03/057170 A1 | 7/2003 |
| WO | WO-03/057650 A1 | 7/2003 |

OTHER PUBLICATIONS

Brown et al, J. Med. Chem. 1994, 27(1), pp. 79-81.*

1995:746537, for Yanagihara et al, JP 07149045.*

1999:558280, for Rahbar et al, Biochemical and Biophysical Research Communications, (1999), 262(3), 651-656.*

Brown et al, Journal of Medicinal Chemistry, 1984, 27(1), pp. 79-81.*

1999:697456 for Rahbar et al, Biochemical and Biophysical Research Communications (1999) 264 (3) 1008.*

1983:71712, for JP patent 57171946.*

Rahbar, Biochemical and Biophysical Research Communications, vol. 262, pp. 651-656 (1999).*

Rahbar, Biochemical and Biophysical Research Communications, vol. 264, p. 1008 (1999).*

Brown et al, J. Med. Chem. 1984, vol. 27, pp. 79-81.*

Brown et al., Receptor Binding Sites of Hypoglycemia Sulfonylureas and Related.

Leone-Bay, A., "N-Acylated alpha-amino acids as novel oral delivery agents for proteins", Journal of Medicinal Chemistry, vol. 38, pp. 4263-4269 (1995).

Leone-Bay, A., "Microsphere Formation in a Series of Derivatized Alpha-Amino Acids: Properties, Molecular Modeling, and Oral Delivery of Salmon Calcitonin", Journal of Medicinal Chemistry, vol. 38, pp. 4257-4262 (1995).

Ho Koc-Kan, et al., "A Practical Synthesis of -aminoalkanoic acid derivatives from Cycloalkaones" Synthetic Communication, vol. 26, No. 14: 2641-2649 (1996).

Abstract Leone-Bay, A., "4-(4-Salicyloylaminophenyl)butyric Acid as a Novel Oral Delivery Agent for Recombinant Human Growth Hormone" Medi 006, Presented at the American Chemical Society, (Mar. 1996) New Orleans, LA.

Leone-Bay, A., "4-[4-[(2-Hydroxybenzoyl)amino]phenyl]butyric acid as a novel delivery agent for recombinant human growth hormone", Journal of Medicinal Chemistry, vol. 39, pp. 2571-2578 (1996).

Leone-Bay, et al., "The evolution of an oral heparin dosing solution", Drugs of the Future, vol. 22(8), pp. 885-891 (1997).

Ho Koc-Kan, et al., "Solution Phase Preparation of Highly Pure Amide Mixtures Via In-Situ Chlorotrimethylsilane Protection and Activation", Synthetic Communication, vol. 27, No. 5, pp. 883-895 (1997).

Leone-Bay, A., et al., "Acylated non-alpha-amino acids as novel agents for the oral delivery of heparin sodium, USP", Journal of Controlled Release, vol. 50, pp. 41-49 (1998).

Leone-Bay, A., "Synthesis and Evaluation of Compounds that Facilitate the Gastrointestinal Absorption of Heparin", Journal of Medicinal Chemistry, vol. 41, pp. 1163-1171 (1998).

Francia Farmaceutica "y-(o-Hydroxybenzamido)-Butyric Acid", Chem. Abstracts, vol. 10, 114838e (1969).

Picciola, G., "Sintesi di acidi chinazollinonici E Benzossazinonici E Studio Delle Loro Proprieta Antiinfiammaatorie", IT, Il Farmaco, Ed. Sc., vol. 31, No. 9, pp. 655-664 (1976).

Picciola, G., "Synthesis of Quinazolinone and Benzoxazainon Acids and Study of their anti-inflammatory properties", IT, Il Farmaco, Ed. Sc., vol. 31, No. 9, pp. 655-664 (1976).

Picciola, G., "Synthesis of Quinazolinone and Benzoxazainon Acids and Study of their anti-inflammatory properties", Chem Abstract, 86:5402t(1977).

Brown, G., et al. "Receptor Binding Sites of Hypoglycemic Sulfonylureas and Related [(Acylamino)Alkyl] Benzoic Acids", J. Med. Chem. 27, pp. 79-81 (1984).

Amino Yusuke et al., "Phenylalanin Derivatives Enhancing Intestinal Absorption of Insulin in Mice" Chem. Pharm. Bull. 36, pp. 4426-4434 (1988).

Palagiano, F., et al., "Synthesis, Stability and Anticonvulsant Activity of Two New GABA Prodrugs", Pharmazie 52(4): 272-276 (1997).

Drain, D.J. et al.: "Anti-Inflammatory Properties of a Series of Phenyl- and Phenoxy-alkanoic Acids," Journal of Pharmacy and Pharmacology, London, GB, vol. 22, No. 9, 1970, pp. 684-693, XP008034324.

Database CA 'Online! Chemical Abstracts Services, Columbus, Ohio, US; Yanagihara, Naoto et al: "Thermal recording materials," XP002311920, retrieved from, STN, Database accession No. 123:213336 (1995).

Milstein, S.J. et al.: "Partially unfolded proteins efficiently penetrate cell membranes—implications for oral drug delivery," Journal of Controlled Release, Elsevier Science Publishers B.V. Amsterdam, NL, vol. 53, No. 1-3, Apr. 30, 1998, pp. 259-267, XP004121276.

Leone-Bay, A. et al.,: "N-acylated alpha-amino acids as novel oral delivery agents for proteins," Journal of Medicinal Chemistry, American Chemical Society, Washington, US, vol. 38, No. 21, Oct. 13, 1995, pp. 4263-4269, XP002286601.

* cited by examiner

COMPOUNDS AND COMPOSITIONS FOR DELIVERING ACTIVE AGENTS

This application is a U.S. national phase application under 35 U.S.C. §371 based upon co-pending International Application No. PCT/US01/01274 filed Jan. 12, 2001, which claims the benefit of priority of U.S. Provisional Application Ser. No. 60/175,947 filed Jan. 13, 2000, Ser. No. 60/194,421 filed Apr. 4, 2000 and Ser. No. 60/202,210 filed May 5, 2000. The entire disclosures of the prior applications are incorporated herein by reference. The international application was published in the English language on Jul. 19, 2001 under Publication No. WO 01/51454.

FIELD OF THE INVENTION

The present invention relates to compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention have the following formula:

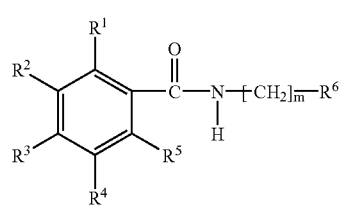

Formula I wherein:
$R^1$, $R^2$, $R^3$, $R^4$, and $R^5$ are independently selected from hydrogen, halogen, —OH, —OCH$_3$, C$_1$–C$_4$ alkyl, —NH$_2$, —NH(CH$_3$), —N(CH$_3$)$_2$, or —NO$_2$;

m is an integer ranging from 0 to 4;

$R^6$ is a phenyl substituted with —O—$R^{7-}$ COOH at the ortho, meta, or para position;

$R^6$ is optionally substituted with one or more members selected from halogen, —OH, —OCH$_3$, C$_1$–C$_4$ alkyl, —NH$_2$, NH(CH$_3$), —N(CH$_3$)$_2$, and —NO$_2$; and $R_7$ is C$_1$–C$_{12}$ alkylene, or a salt thereof.

In one preferred embodiment, $R^1$ is —OH. According to another preferred embodiment, $R^1$ is —OCH$_3$.

In another preferred embodiment, m is 0. According to yet another preferred embodiment, m is 3.

In another preferred embodiment, $R^7$ C$_3$–C$_9$ alkylene. According to yet another preferred embodiment, $R^7$ is C$_3$–C$_7$ alkylene.

In another preferred embodiment, $R^1$ is —OH, $R^6$ is a phenyl, —O—$R^7$—COOH in the ortho position More preferably, $R^6$ is a phenyl, with a Cl substituent para to the —O—$R^7$—COOH. More preferably, $R^7$ is a C$_3$–C$_7$ alkylene. More preferably, m=0.

In another preferred embodiment, $R^1$ is —OCH$_3$, m is from 1 to 3, $R^6$ is a phenyl substituted with —O—$R^7$—COOH at the para position. More preferably, $R^7$ is a C$_3$–C$_7$ alkylene.

Preferred compounds include, but are not limited to, the monosodium and disodium salts of the compounds of formula I above.

Special mention is made of compounds having the formula:

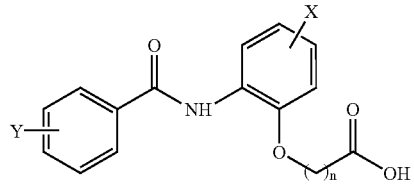

Formula II wherein n is an integer from 1 to 12;

X is one or more of the following independently selected substituents: halogen, —OH, —OCH$_3$, C$_1$–C$_4$ alkyl, —NH$_2$, —N(CH$_3$)$_2$, or —NO$_2$;

Y is one or more of the following independently selected substituents: halogen, OH, OCH$_3$, C$_1$–C$_4$ alkyl, NH$_2$, N(CH$_3$)$_2$, or NO$_2$, or salts thereof.

Preferably, n is an integer from 3 to 9 and more preferably from 3 to 7.

According to one preferred embodiment, X is a Cl at the 4-position of the phenyl group.

According to another preferred embodiment, Y is —OH at the 2-position of the phenyl group.

More preferred compounds comprise one or more of the following:

Compound 1

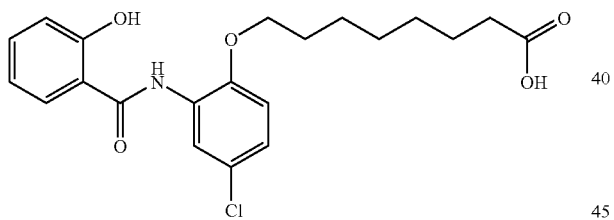

Compound 2

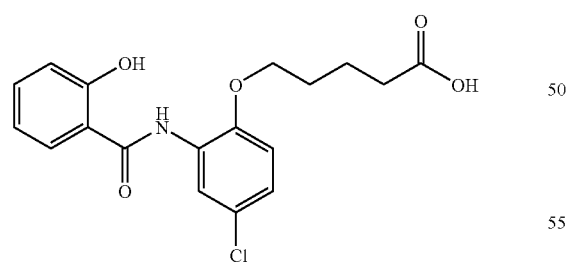

Compound 3

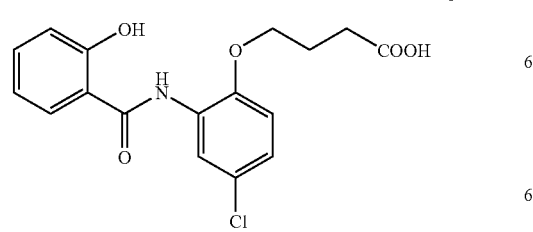

-continued

Compound 4

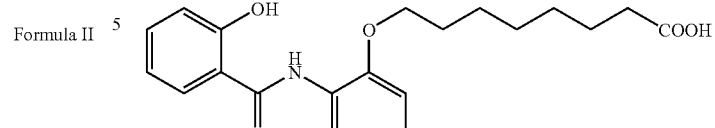

Compound 5

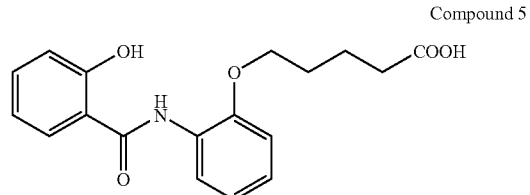

Compound 6

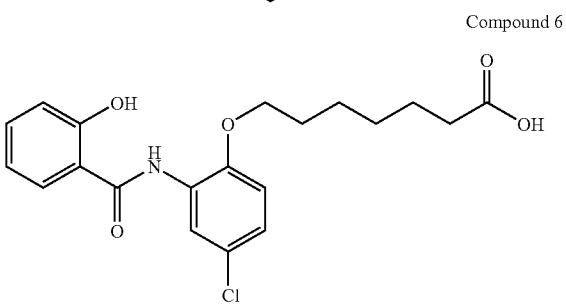

Compound 7

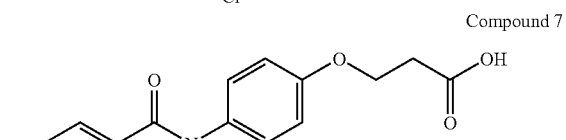

Compound 8

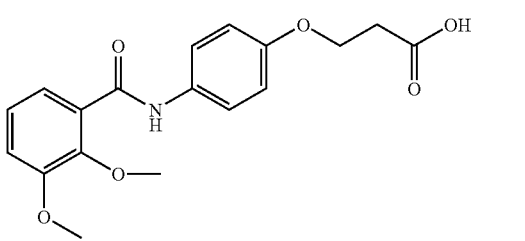

Compound 9

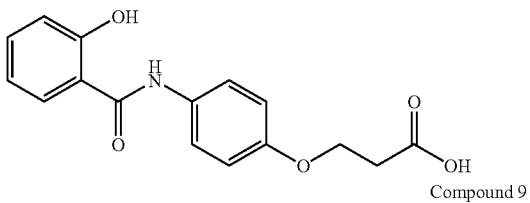

Compound 10

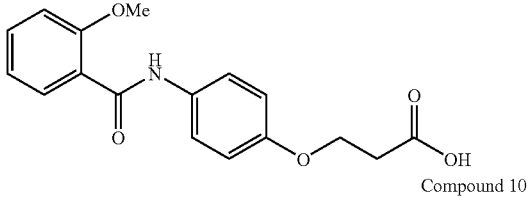

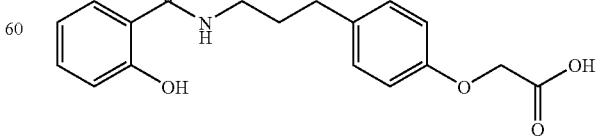

or salts thereof.

The invention also provides a composition comprising at least one of the delivery agent compounds of the formulae I and II, 1–10, above, or salts thereof, or mixtures thereof, and at least one active agent. These compositions deliver active agents to biological systems in increased or improved bioavailability of the active agent compared to administration of the active agent without the delivery agent compound.

Also provided are dosage unit forms comprising the compositions. The dosage unit form may be in the form of a liquid or a solid, such as a tablet, capsule or particle, including a powder or sachet.

Another embodiment is a method for administering an active agent to an animal in need of the active agent by administering to the animal a composition comprising at least one of the delivery agent compounds above and the active agent. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formula above and at least one active agent.

DETAILED DESCRIPTION OF THE INVENTION

Delivery Agent Compounds

The delivery agent compounds may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates. The term "solvate" as used herein includes, but is not limited to, a molecular or ionic complex of molecules or ions of a solvent, such as ethanol, with ions or molecules of the compounds of the present invention.

Salts of the delivery agent compounds of the present invention may be prepared by methods known in the art. For example, sodium salts may be prepared by dissolving the delivery agent compound in ethanol and adding aqueous sodium hydroxide.

In general, the compounds of the present invention may be prepared using the following method.

The appropriately substituted amino-phenol (such as 2-amino-phenol) and the appropriate alkylating agent are mixed in potassium hydroxide (KOH) and dimethyl sulfoxide (DMSO) for 2 hours at room temperature, then poured into distilled water and extracted with ethyl acetate (EtOAc). The combined organic layers are washed with water, dried with magnesium sulfate ($MgSO_4$), and filtered. The solvent is evaporated in vacuo to give a crude product, which may be purified by methods known in the art, such as medium pressure liquid chromatography (MPLC) utilizing 10% EtOAc in hexanes as the eluting solvent, to yield an intermediate ester.

The intermediate ester is dissolved in tetrahydrofuran (THF), flushed with nitrogen and cooled to about 0° C. Triethylamine and then the appropriately substituted benzoyl chloride dissolved in THF (100 mL) are added slowly to the solution containing the intermediate ester. The mixture is allowed to warm up to room temperature and is stirred overnight, monitoring the progress of the reaction by thin-layer chromatography. Work-up of the reaction is done by addition of 3% HCl solution. The phases are separated, and the organic layer is washed with 3% HCl, water and then a saturated solution of NaCl. The organic layer is dried with $MgSO_4$, filtered, and the solvent evaporated in vacuo.

A 10% aqueous solution of sodium hydroxide (NaOH) is added to this product and the mixture stirred for 2 hours at about 90° C., then cooled and diluted with water. The solution is and acidified to about a pH of 6 or lower. The product separates from solution and is collected by filtration, washed generously with water, and dried overnight under vacuum at 40° C. to yield the product as a crystalline powder.

The term "halogen" as used herein, unless otherwise indicated, fluoro, chloro, bromo and iodo. The term "alkyl" as used herein, unless otherwise indicated, includes saturated monovalent hydrocarbon radicals and may be straight, branched or cyclic. Such alkyl groups may include one or two double or triple bonds. It is understood that for cyclic alkyls at least three carbon atoms are required to form the ring.

The solvate may be prepared by dissolving the compound of the present invention in a solvent, such as ethanol, and then reacting the mixture with a molar excess of a salt, such as a sodium containing salt (e.g. sodium hydroxide). For example, to prepare an ethanol solvate of a disodium salt of a compound of the present invention, at least about two molar equivalents of a monosodium containing salt are added to a mixture of the compound and ethanol. The solvate may be recovered by methods known in the art.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastrointestinal mucosa and/or are susceptible to chemical cleavage by acids and enzymes in the gastrointestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (e.g. sodium or disodium chromoglycate); vancomycin; desferrioxamine (DFO); bisphosphonates, including alendronate, tiludronate, etidronate, clodronate, pamidronate, olpadronate, and incadronate; parathyroid hormone, including its fragments; antimicrobials, including antibiotics, anti-bacterials (non-limiting examples of antibiotics include gram-positive acting, bacteriocidal, lipopeptidal and cyclic peptidal antibiotics, such as daptomycin and analogs thereof) and anti-fungal agents; vitamins; analogs, fragments, mimetics or polyethylene glycol (PEG)-modified derivatives of these compounds; or any combination thereof.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternatively, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof. Non-limiting examples of such ingredients are described in Remingtons Pharmaceutical Sciences, 18th Ed., Mack Publishing Co. (1990), hereby incorporated by reference.

The compounds and compositions of the subject invention are useful for administering biologically or chemically active agents to any animals, including but not limited to birds, such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference ($54^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
|---|---|
| Growth hormones | Growth disorders |
| Interferons, including α, β and γ | Viral infection, including chronic cancer and multiple sclerosis |
| Interleukin-1; interleukin-2 | Viral infection; cancer |
| Insulin; Insulin-like growth factor (IGF-1) | Diabetes |
| Heparin | Thrombosis; prevention of blood coagulation |
| Calcitonin | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments | Osteoporosis; Diseases of the bone |
| Antimicrobials | Infection including gram-positive bacterial infection |
| Vitamins | Vitamin deficiencies |
| Bisphosphonates | Osteoporosis ; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

EXAMPLE 1

Compound Preparation

Preparation of Compound 1

A 500-mL round-bottomed flask was charged with KOH (16.1 g, 270 mmol) and DMSO (160 mL). 2-Amino-4-chlorophenol (13.6 g, 94.7 mmol) was added to the mixture, followed by ethyl 8-bromooctanoate (24.0 g, 95.5 mmol), and the resulting mixture was stirred for 2 hours at room temperature. The mixture was poured into 200 mL of distilled water. The solution was extracted with EtOAc (2×200 mL). The organic layers were combined, washed once with water, dried with $MgSO_4$, and filtered. The solvent was evaporated in vacuo to give a crude product, which was a thick, brown liquid. The product was purified by medium pressure liquid chromatography (MPLC) utilizing 10% EtOAc in hexanes as the eluting solvent, to yield an intermediate ester as a light brown liquid (17.1 g, 54.5 mmol, 38% yield).

The intermediate ester (3.37 g, 17 mmol) was dissolved in THF (150 ml) and charged to a 500-mL round-bottomed flask equipped with an addition funnel. The system was flushed with nitrogen and cooled to 0° C. with an ice bath. Triethylamine (3.0 mL, 21.2 mmol) was added slowly via a syringe. O-Acetyl salicyloyl chloride (3.37 g, 17 mmol) was dissolved in THF (100 mL) and charged to the addition funnel and added slowly over 30 minutes to the ester mixture. The solution slowly turned cloudy. The mixture was allowed to warm up to room temperature and was stirred overnight. The progress of the reaction was monitored by thin-layer chromatography. Work-up of the reaction was done by addition of 3% (v/v) HCl solution (100 mL). The phases were separated, and the organic layer was washed once more with 3% (v/v) HCl (100 mL), followed by $H_2O$ (100 mL) and a saturated solution of NaCl (100 mL). The organic layer was dried with $MgSO_4$, filtered, and the solvent was evaporated in vacuo.

A 10% (w/w) aqueous solution of NaOH (68 mL) was added to the crude product isolated above and the mixture was stirred for 2 hours at 90° C. using an oil bath. The solution was cooled and diluted with water (100 mL), and acidified to a pH of about 6. A white precipitate was formed, collected by filtration, washed generously with water, and dried overnight under vacuum at 40° C. to yield Compound 1 as a fine, white crystalline powder (4.60 g, 11.3 mmol, 66% yield); mp 152–153° C.; Analysis calculated for $C_{21}H_{24}ClNO_5$: % C, 62.14 (calculated), 62.20 (found); % H, 5.96 (calculated), 5.81 (found); % N, 3.45 (calculated), 3.26 (found). $^1$H NMR Analysis (DMSO-$d_6$): δ 1.27–1.53, 1.77–1.91, 2.15–2.20, (4.05–4.09, 6.97–7.10, 7.41–7.47, 8.01–8.05, 8.56–8.57, 11.0, 11.6, 12.0. Compounds 2, 3, 4, and 5 were prepared by this method using the appropriate starting materials. Compound 6 can also be prepared by this method using the appropriate starting materials.

Compound 2 Melting point: 166–169° C. Combustion analysis: % C, 59.43 (calculated), 59.37 (found); % H, 4.99 (calculated), 4.96 (found); % N, 3.85 (calculated), 3.59 (found); % Cl, 9.75 (calculated), 9.74 (found). $^1$H NMR Analysis (d6-DMSO): δ 11.80–12.0, 11.00, 8.58, 8.02–8.05, 7.41–7.47, 7.06–7.10, 6.98–7.03, 4.06–4.11, 2.31–2.36, 1.68–1.86.)

Compounds 3: Melting point: 231–234° C. Combustion analysis: % C, 58.38 (calculated), 58.13 (found); % H, 4.61 (calculated), 4.67 (found); % N, 4.00 (calculated), 3.91 (found); % Cl, 10.14 (calculated), 10.10 (found). $^1$H NMR Analysis: (d6-DMSO): δ11.80–12.0, 11.00, 8.02–8.06, 7.41–7.47, 7.06–7.10, 6.98–7.03, 4.08–4.13, 2.44–2.52, 2.00–2.10.

Compound 4: Melting point: 122–124 C. Combustion analysis: % C, 67.91 (calculated), 67.77 (found); % H, 6.78 (calculated), 6.83 (found); % N, 3.77 (calculated), 3.78 (found). $^1$H NMR Analysis: (d6-DMSO): δ 11.80–12.0 (br, s, 1H), 11.00 (s, 1H), 8.41–8.44 (m, 1H), 8.01–8.04 (dd, 1H), 7.38–7.44 (m, 1H), 7.04–7.08 (m, 3H), 6.91–7.00 (m, 2H), 4.03–4.08 (t, 2H), 2.15–2.19 (t, 2H), 1.78–1.83 (m, 2H), 1.26–1.50 (m, 8H).

Compound 5: Melting point: 147–149 C. Combustion analysis: % C, 54.22 (calculated), 54.15 (found); % H, 5.79 (calculated), 5.74 (found); % N, 5.75 (calculated), 5.66 (found). $^1$H NMR Analysis: (d6-DMSO): δ 11.80–12.0 (br. s, 1H), 11.00 (s, 1H), 8.44–8.47 (m, 1H), 8.02–8.05 (dd, 1H), 7.39–7.45 (m, 1H), 7.01–7.09 (m, 3H), 6.91–6.99 (m, 2H), 4.05–4.10 (t, 2H), 2.31–2.36 (t, 2H), 1.68–1.87 (m, 4H).

Preparation of Compound 8

Step A: 4-aminophenol (10.00 g, 0.0917), dioxane (175 ml), and water (90 ml) were added to a 1 liter, round, bottomed flask fitted with a magnetic stir bar, addition funnel and argon purge. The reaction mixture was cooled in an ice/water bath and dropwise addition of a 1 N NaOH solution (91.7 ml) was made to the reaction mixture over a period of 10 minutes. Di-t-butyl dicarbonate (19.00 g, 0.0917 mol) was dissolved in dioxane (30 ml) and this solution was placed in the addition funnel. Dropwise addition of this solution was made over a 45 minute period. The ice bath was removed and the reaction mixture was allowed to come to ambient temperature overnight. After stirring overnight, dioxane was removed in vacuo and ethyl acetate was added to the reaction mixture. 0.5M $H_2SO_4$ solution was added until the pH of the aqueous layer was 2. The ethyl acetate layer was separated off and the aqueous layer was extracted with two additional portions of ethyl acetate. The combined ethyl acetate layers were decolorized with activated carbon, were dried with sodium sulfate and concentrated in vacuo to yield a brown solid which was washed with warm hexanes. The resulting 4-N-(tert-butyloxycarbonyl)-1-hydroxy benzene was isolated in a yield of 14.82 g.

A portion of the 4-N-(tert-butyloxycarbonyl)-1-hydroxy benzene (7.0 g, 0.0335 mol) and acetone (60 ml) were placed in a 250 ml round bottomed flask fitted with argon purge, magnetic stir bar and cold water condenser. 3-bromobenzylpropyl ether (6.50 ml, 0.0368 mol) and potassium carbonate (4.62 g, 0.0335 mol) were added and heating of the reaction mixture was started. After refluxing for 4 days, heating of the reaction mixture was stopped and deionized water (100 ml) was added. This mixture was extracted with 2 portions of diethyl ether (100 ml portions). The combined ether layer was then extracted with 2 portions of 2N NaOH solution (100 ml portions). The ether layer was dried with sodium sulfate and concentrated in vacuo leaving a tan solid. The tan solid was recrystallized from hexanes to yield 3-(4-N-(tert-butyloxycarbonyl)phenoxy)-1-benzyloxy propane (8.2 g).

3-(4-N-(tert-butyloxycarbonyl)phenoxy)-1-benzyloxy propane (12.75 g, 0.0357 mol), prepared as written above, was placed in a 500 ml round bottomed flask fitted with an argon purge and a magnetic stir bar. The reaction mixture was sparged with argon for about 30 minutes before 10% palladium on activated carbon (0.75 g) was added to the reaction mixture. The reaction vessel was evacuated and a balloon containing hydrogen was placed atop the reaction vessel. After stirring two days an additional portion of 10% palladium on activated carbon (0.25 g) was added. The flask was again evacuated and a balloon containing hydrogen again was placed atop the flask. This mixture stirred for 4 additional days under hydrogen (refilling the balloon as necessary). The reaction mixture was then filtered and the filtrate was concentrated in vacuo yielding 3-(4-N-(tert-butyloxycarbonyl)phenoxy)propane-1-ol as a white solid in a yield of 9.47 g.

3-(4-N-(tert-butyloxycarbonyl)phenoxy)propane-1-ol (9.25 g, 0.0346 mol), which was prepared as described above, was added to a 250 ml, round, bottomed flask fitted with an argon purge and a magnetic stir bar. Pyridinium dichromate (45.59 g, 0.1213 mol) was added and the reaction was allowed to stir at ambient temperature overnight. The reaction mixture was then poured into 500 ml of water and was extracted with three, 200 ml portions of ethyl acetate. The combined ethyl acetate portions were washed with 100 ml of 0.5M $H_2SO_4$, and then were extracted with 100 ml of 2N, NaOH solution. The NaOH layer was then acidified with 2N HCl solution, which caused a gray solid to precipitate. 3-(4-N-(tert-butyloxycarbonyl)phenoxy)propionic acid was isolated in a yield of 3.26 g.

3-(4-N-(tert-butyloxycarbonyl)phenoxy)propionic acid prepared above (3.25 g, 0.01157 mol) and dioxane (30 ml) were placed in a 100 ml round, bottomed flask. The reaction mixture was filtered and the filtrate was placed in another 100 ml round bottomed flask fitted with an argon purge, and magnetic stir bar. 4M HCl in dioxane (20 ml) was added and the mixture was allowed to stir at ambient temperature. After stirring overnight, the reaction mixture was filtered and a white solid was isolated. The filtrate was set-aside for three days and more solid was noted to have precipitated. This solid was isolated by filtration and was combined with the earlier isolated solid. 4M HCl in dioxane (10 ml) was added to the solids. After stirring overnight at ambient temperature, additional solid was noted to have precipitated. This was also isolated by filtration and combined with the earlier isolated solids. This combined solid was dried in vacuo and 3-(4-aminophenoxy)propionic acid was isolated in a yield of 2.08 g.

3-(4-aminophenoxy)propionic acid prepared above (1.95 g, 0.0108 mol) was placed in a 250 ml round bottomed flask fitted with a condenser, argon purge, and magnetic stir bar. Dichloromethane was added and a tan slurry was formed. Trimethylsilyl chloride (2.74 ml, 0.0215 mol) was added to the reaction mixture and heating to reflux was started. After 1.5 hours, heating was discontinued and the reaction mixture was cooled in an ice/water bath. Triethyl amine (2.25 ml, 0.0162 mol) was added. Acetylsalicyloyl chloride (2.03 g, 0.0102 mol) was dissolved in dichloromethane (10 ml). This solution was placed in an addition funnel atop the flask, which had replaced the condenser atop the flask. Dropwise addition of the acetylsalicyloyl chloride solution was then made over a period of 15 minutes. This mixture was allowed to stir an additional 30 minutes before the ice bath was removed and the reaction was allowed to come to room temperature overnight. The methylene chloride was then removed in vacuo. 2N NaOH (70 ml) was then added and this mixture was allowed to stir for approximately 30 minutes before the reaction mixture was acidified with 2M $H_2SO_4$. A tan solid precipitated which was isolated by filtration, taken up in ethyl acetate and washed with 2, 50 ml portions of 2N HCl solution. The ethyl acetate layer was dried with sodium sulfate and was concentrated in vacuo. The resulting tan solid was recrystallized from ethanol/water solution, washed with water resulting in a tan solid.

Step B: This solid was taken up in ethyl alcohol in a 250 ml Erlenmeyer flask. The mixture was heated until the solid was dissolved. The mixture was then hot filtered and 10N NaOH solution (0.64 ml, 0.0064 mol) was added to the filtrate to form a filtrate. After stirring the mixture for several minutes, approximately half of the ethanol was removed in vacuo. Heptane (75 ml) was added to the resulting slurry. The mixture was filtered, dried further in vacuo and a solid was isolated. The solid was taken up in a NaOH/H$_2$O mixture. This solution was acidified with 2M H$_2$SO$_4$. The white solid which precipitated was isolated by filtration, recrystallized from a 1:1, ethanol:water mixture and was dried under vacuum.

Step C: The product, 3-(4-salicyloylamino)phenoxy propionic acid was isolated in a yield of 1.40 g.

Compound 8: Melting point: 165–167° C. Combustion analysis: % C, 63.79 (calculated), 63.58 (found); % H, 4.98 (calculated), 4.92 (found); % N, 4.65 (calculated), 4.57 (found). $^1$H NMR Analysis: (d$_6$-DMSO): δ 12.4, (COOH); δ 12.00, (OH); δ 10.3, s, 1H, (NH); δ 7.95, (CH aromatic ring alpha to amide); δ 7.55, (CH aromatic ring alpha to ether); δ 7.40, (CH aromatic ring para to amide); δ6.91, (CH aromatic ring meta to ether, and CH's ortho and para to hydroxy); δ 4.13, (CH$_2$ alpha to ether); δ 2.65, (CH$_2$ alpha to carboxylic acid).

Preparation of Compound 9

Compound 9 was prepared by the procedure described for the preparation of compound 8, however step B was omitted and O-anisoyl chloride was used in place of acetylsalicyloyl chloride.

Compound 9: Melting point: 154–158° C. Combustion analysis: % C, 64.76 (calculated), 64.70 (found); % H, 5.40 (calculated), 5.51 (found); % N, 4.44 (calculated), 4.24 (found). $^1$H NMR Analysis: (d$_6$-DMSO): δ 12.4, (COOH); δ 10.0, s, 1H, (NH); δ 7.61, (CH aromatic ring alpha to amide, and CH's aromatic ring alpha to ether); δ 7.45, (CH aromatic ring meta to methoxy); δ 7.15, d, (CH aromatic ring alpha to methoxy); δ 7.03, (CH aromatic ring para to ether); δ 4.10, (CH$_2$ alpha to ether); δ 3.85, (CH$_3$); δ2.65, (CH$_2$ alpha to carboxylic acid).

Preparation of Compound 7

Compound 7 was prepared by the procedure described for the preparation of compound 8. however step B was omitted and 2,3-dimethoxybenzoyl chloride was used in place of acetylsalicyloyl chloride.

Compound 7: Melting point: 135–137° C. Combustion analysis: % C, 62.61 (calculated), 62.31 (found); % H, 5.51 (calculated), 5.57 (found); % N, 4.06 (calculated), 3.95 (found). $^1$H NMR Analysis: (d$_6$-DMSO): δ 12.3, (COOH); δ 10.1, (NH); δ 7.60, (CH's aromatic ring alpha to ether); δ 7.09, (CH's aromatic ring ortho, meta and para to the 3-methoxy group); δ 6.88, dd, 2H, (CH aromatic ring meta to ether); δ 4.13, (CH$_2$ alpha to ether); δ 3.85, (CH$_3$ 2-methoxy group); δ 3.78, s, 3H, (CH$_3$ 3-methoxy group); δ 2.66, t, 2H, (CH$_2$ alpha to carboxylic acid)

Preparation of Compound 10

3-(4-Hydroxyphenyl)-1-promanol (20.0 g, 0.135 mole) and potassium carbonate (22.2 g, 0.162 mole) were stirred in acetone/water (150 mL/15 mL) in a 500 mL round bottom flask equipped with a condenser, oil bath and a magnetic stirrer. Ethyl bromoacetate was added dropwise and the flask was heated to reflux for 18 hours. The reaction was cooled to room temperature and the reaction concentrated in vaccu. The residue was dissolved in ethyl acetate and washed with water, 1N hydrochloric acid and water again. The organics were dried over sodium sulfate, filtered and concentrated in vaccu. The structure of intermediate compound I, was confirmed by $^1$H NMR and used without further purification, 30.29 g, 94.3% yield.

Intermediate compound, I (30.29 g, 0.127 mole) was dissolved in methylene chloride (100 mL) in a round bottom flask equipped with an addition funnel and an argon inlet/bubbler. The solution was cooled in an ice bath. Triethylamine (19.47 mL, 0.139 mole) was added dropwise over 5 minutes. Tosyl chloride (21.26 g, 0.127 mole) was dissolved in methylene chloride and added dropwise over 20 minutes to the reaction flask. The reaction was allowed to warm to room temperature and monitored by HPLC. Triethylamine and Tosyl chloride were added and the reaction monitored to completion. The mixture was concentrated in vaccu and the residue dissolved in ethyl acetate. The solution was washed with hydrochloric acid (2×100 mL, 1 N) and saturated sodium bicarbonate (6×100 mL). The organics were dried over sodium sulfate and concentrated in vaccu. The structure of intermediate compound II, was confirmed by 1H NMR and used without further purification, 29.15 g, 60% yield.

In a 1 neck, 250 mL flask carsalam (4.22 g, 0.026 mole), intermediate compound II (10.0 g, 0.026 mole), N,N-dimethylacetamide (100 mL), and sodium carbonate (3.03 g, 0.0286 mole) were heated to 90° C. under nitrogen for 20 hours. The reaction was cooled to room temperature and filtered to remove inorganics. Water (100 mL) was added and the solution extracted with ethyl acetate (3×100 mL). The organics were combined and concentrated in vacuo. The residue was stirred in sodium hydroxide (2N) and 1,4-dioxane for 2.5 hours and then acidified with concentrated hydrochloric acid. The resulting solids were recovered by filtration and dried in vacuo over phosphorous pentoxide to yield compound 10.

Compound 10: Melting point: 124–126.5° C. Combustion analysis for C$_{18}$H$_{19}$O$_5$N: % C, 65.64 (calculated), 65.32 (found); % H, 5.81 (calculated), 5.89 (found); % N, 4.25 (calculated), 4.15 (found). $^1$H NMR Analysis: (300 MHz, d$_6$-DMSO): δ 13.0; 8.85; 7.85; 7.40; 7.15; 6.85; 4.60; 3.30; 2.6; 1.8.

Preparation of the Ethanol Solvate of the Disodium Salt of Compound 1

In a 2 L 4-neck flask equipped with condenser, thermocouple and recorder, variac (variable transformer), heating mantle, motorized stirrer, and addition funnel, 2-amino-4-chlorophenol (200 g, 1.30 mole, available from Aldrich Chemical Company, Inc. of Milwaukee, Wis., was stirred in water (500 ml). Acetic anhydride (171 g, 1.68 mole) was added to the reaction flask over 10 minutes. The reaction was heated to reflux for 30 minutes and then cooled to room temperature. The resulting slurry was vacuum filtered and solids washed with water yielding brown solids which were dried in vacuo at 50° C. (249.2 g of N-acetyl-2-amino-4-chlorophenol; 97% yield; 95.4% by gas chromatography (GC)).

In a 2 L, 4-neck flask equipped with condenser, thermocouple and recorder, nitrogen inlet/bubble, motorized stirrer, and addition funnel, ethanol (200 mL) was charged. Sodium (9.5 g, 0.412 mole) was added, after washing with kerosene, over 30 minutes keeping the reaction temperature below 60° C. The reaction was stirred until all of the sodium dissolved (about 90 minutes), while allowing the reaction to cool to 25° C. 61.25 g (0.33 mole) N-acetyl-2-amino-4-chlorophenol was dissolved in ethanol (350 mL) at 70° C. and added to the sodium solution by cannula. Ethyl 8-bromooctanoate (103 g, 0.412 mole) (available from Riedel-de Haen, Seelze, Germany) was then added to the reaction by addition funnel. The reaction was heated to reflux for about 18.5 hours. After cooling to room temperature, the reaction was filtered and the filtrate condensed in vacuo. The resulting brown semisolid was stirred with heptane (600 mL) for several hours, filtered and dried in vacuo yielding 120.8 g of 2-N-acetylamino-4-(chlorophenoxy)ethyl octanoate as a solid, 100% yield.

In a 5 liter, 4-neck flask equipped with a motorized stirrer, thermometer, THERM-O-WATCH® heat controller (available from I²R, Cheltenham, Pa.), heating mantle, and a nitrogen inlet/bubbler, sodium hydroxide (240.0 g, 6.0 mole) was dissolved in ethanol (120 mL) at 46.5° C. 12.0 g (0.337 mole) 2-N-acetylamino-4-(chlorophenoxy)ethyl octanoate was added to the solution and the flask was heated to 80° C. for about 13 hours. The hydrolysis was followed by HPLC. Ethanol (347.8 mL) was distilled off and the reaction was cooled to 25° C. producing solids. Concentrated hydrochloric acid (469.1 mL) was added to the flask dropwise to a pH of 4.65 keeping the temperature below 25° C. with an ice bath. Brown solids were filtered off and washed with water yielding 82.93 g (86% yield) 8-(2-amino-4chloro-phenoxy) octanoic acid. The structure was verified by NMR. A second batch of 81.33 g of the same compound was made by the same method.

In a 3 liter 4-neck flask equipped with motorized stirrer, ice bath, addition funnel, condenser and thermometer, dry methanol (500 mL) was cooled to 2° C. Acetyl chloride (52.56 g, 0.669 mole) was added dropwise to the methanol and the solution was stirred for an additional 15 minutes. 159 g (0.558 mole) 8-(2-amino-4-chloro-phenoxy)octanoic acid was dissolved in dry methanol (500 mL) and slowly added to the reaction flask. After stirring for 15 minutes the ice bath was removed and the flask heated to reflux for 3 hours. The solution was concentrated in vacuo yielding 187 g (100%) of methyl (8-(2-amino-4-chloro-phenoxy)octanoate.HCl) as a light brown solid. The structure was confirmed by NMR.

In a 3 liter 4-neck flask equipped with motorized stirrer, addition funnel and thermometer, 100 g (0.332 mole) methyl (8-(2-amino-4-chloro-phenoxy)octanoate.HCl) was stirred in THF (500 mL) and triethylamine (70.55 g, 0.697 mole) was added dropwise at 5° C. Acetylsalicyloyl chloride (65.98 g, 0.332 mole) dissolved in THF (250 mL) was then added to the reaction over 30 minutes. After an additional 15 minutes at 5° C. the reaction was warmed to room temperature and monitored by HPLC. Sodium hydroxide (2N, a total of 950 mL) was added to the reaction flask and the hydrolysis followed by HPLC. The reaction was cooled to 5° C. with an ice bath and concentrated hydrochloric acid (170 mL) was added dropwise to the reaction keeping the temperature below 20° C. to a final pH of 4.0. The THF was distilled off and the resulting tan solid filtered off and air-dried, yielding 117.91 g (87.5% yield) of 8-[(N-Salicyloyl-2-amino-4-chloro)phenoxyl]octanoic acid (Compound III). The structure was confirmed by NMR and elemental analysis (calculated for $C_{21}H_{24}NO_5Cl$: C, 62.14; H, 5.96; N, 3.45; analyzed: C, 61.92;H, 5.91; N, 3.26).

In a 2 liter 3-neck flask equipped with a motorized stirrer, heating mantle, thermometer, nitrogen inlet/bubbler and addition funnel, 117.91 g Compound III was stirred in ethanol (1 L) and heated to 75° C. for 30 minutes. The temperature was lowered to 70° C. and sodium hydroxide in ethanol (11.3 wt %, 199.7 mL) was added to the solution and stirred for 30 minutes. Ethanol (970 mL) was distilled off and the reaction cooled slightly. The molten mass was poured into a crystallizing dish and dried at 80° C., full vacuum grinding of solids after they formed, yielding (130.36 g (97.4%) disodium 8-(N-salicyloyl-2-amino-4-chloro)phenoxy)octanoate, ethanol solvate (Compound I ethanol solvate). The structure of the ethanol solvate was verified by elemental analysis: calculated for $C_{23}H_{28}NO_6Na_2Cl.1.3664\ H_2O$: C, 55.31; H, 5.19; H, 2.80; Na, 9.21; found: C, 54.4; H, 5.42; N, 2.90; Na, 7.98. The structure of the ethanol solvate was verified by $^1H$ NMR (300 MHz, DMSO-$d_6$): δ14.8, 8.70, 7.7, 6.9, 6.55,6.2, 4.0, 4.4 3.45, 1.4, 1.24.4, ethanol; 4.4, 3.45, 1.05. Melting point >250° C. (limit of instrument used).

EXAMPLE 2

Pulmonary Insulin

Dosing compositions of delivery agent compound and human insulin in water were prepared. Typically, deionized water was added to 1.5 mg of delivery agent compound to bring the volume to 1.0 ml, and the solution was vortexed. Either the sodium salt of the delivery agent compound was used or the free acid was converted to the sodium salt by stirring the resultant solution and adding one equivalent of sodium hydroxide (10 N) and diluting with water. The solution was vortexed, then heated (about 37° C.) and sonicated. The pH was adjusted to between about 7.0 to 8.5 with NaOH or HCl.

75 µl human insulin stock solution (2 mg/ml) was added to the solution. The human insulin stock solution was prepared as follows. To 0.02 g human insulin was added 3 ml HCl solution (pH=3) in deionized water, the pH of the resulting solution was brought to about 2.6 with HCl and NaOH was added until the solution was clear. The pH was then raised to 7.6 using NaOH and HCl. The final volume was brought to 10 ml with pH 7.5 deionized water so that the final pH was 7.59. Water was added to bring the total volume to 2.0 ml, and the solution was gently inverted several times. The final delivery agent compound dose, insulin dose and volume dose amounts are as listed below in the tables.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. Typically, a dosing group of five rats was administered one of the dosing solutions. A control group of five animals was dosed with insulin alone. A tracheal instillator for rodents, equipped with light (available from Penn Century, Inc., Pittsburgh, Pa.) was filled with dosing solution and inserted down the throat until the needle went into the trachea (confirmed visually). Solution was administered by pressing the plunger.

Blood samples were collected serially from the tail artery, typically at time=5, 15, 30, 60 and 120 minutes. Serum insulin levels were determined with an Insulin ELISA Test Kit (Kit # DSL-10–1600 from Diagnostic Systems Laboratories, Inc., Webster, Tex.). The results from the five rats in each dosing group were averaged for each time point. The maximum is reported below in Table 1.

Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to obtain a clear solution using 40 ml concentrated HCl, 25 ml 10N NaOH and 50 ml 1N NaOH) was added to the solution and mixed by inverting. The solution was used in the dosing protocol immediately, or alternatively, the solution was placed in a 37° C. water bath for one hour prior to dosing. The final delivery agent compound dose, insulin dose and dose volume amounts are listed below in Table 1.

The typical dosing and sampling protocols were as follows. Male Sprague-Dawley rats weighing between about 200–250 g were fasted for 24 hours and administered ketamine (44 mg/kg) and chlorpromazine (1.5 mg/kg) 15 minutes prior to dosing and again as needed to maintain anesthesia. A dosing group of five rats was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the the test kit. Serum human insulin concentrations (µU/ml) were measured for each time point for each of the five rats in each dosing group. The five values for each time point were averaged and the results plotted as serum insulin concentration versus time. The maximum of the averaged values is reported below in Table 1. Previous experiments revealed no measurable levels of human insulin following oral dosing with human insulin alone.

TABLE 1

Pulmonary/Oral Delivery of Insulin

| Compound | Method of Admistration | Volume Dose (ml/kg) | Compound Dose (mg/kg) | Insulin Dose (mg/kg) | Mean Peak Serum Insulin (insulin + Compound) (pg/ml ± SD) (SE) |
|---|---|---|---|---|---|
| 1 | Pulmonary | 0.4 | 0.3 | 0.03 | 73.19 ± 41.6 |
| 1 | Pulmonary | 0.4 | 0.06 | 0.03 | 156.04 ± 87.02 |
| 1 | Pulmonary | 0.4 | 0.15 | 0.03 | 119.89 ± 29.57 |
| 1 | Pulmonary | 0.4 | 0.3 | 0.03 | 151.50 ± 84.63 |
| 1 | Pulmonary | 0.4 | 0.06 | 0.03 | 200.27 ± 87.14 |
| 1 | Pulmonary | 0.4 | 0.15 | 0.03 | 185.09 ± 128.11 |
| 1 | Pulmonary | 0.4 | 0.3 | 0.03 | 129.44 ± 17.49 |
| 1 | Pulmonary | 0.4 | 0.06 | 0.03 | 73.37 ± 19.93 |
| 1 | Pulmonary | 0.4 | 0.03 | 0.03 | 181.80 ± 197.67 |
| 1 | Pulmonary | 0.4 | 0.15 | 0.03 | 93.56 ± 49.84 |
| 1 | Pulmonary | 0.4 | 0.06 | 0.03 | 122.35 ± 96.64 |
| 1 | Pulmonary | 0.4 | 0.03 | 0.03 | 103.73 ± 33.96 |
| 1 | Pulmonary | 0.4 | 0.07 | 0.03 | 128.10 ± 36.31 |
| 1 | Pulmonary | 0.4 | 0.3 | 0.03 | 123.08 ± 40.28 |
| 1 | Pulmonary | 0.4 | 0.3 | 0.03 | 87.02 ± 26.09 |
| 2 | Pulmonary | 0.4 | 0.3 | 0.03 | 11.6 ± 2.27 |
| 2 | PO | 1 | 200 | 0.5 | 5.9 ± 7.94 |
| 3 | PO | 1 | 200 | 0.5 | 110.59 ± 11.84 |
| 4 | PO | 1 | 200 | 0.5 | 6.56 ± 9.22 |
| 4 | PO | 1 | 200 | 0.5 | 5.90 ± 7.90 |
| 5 | PO | 1 | 200 | 0.5 | 45.45 ± 74.04 |
| 5 | PO | 1 | 200 | 0.5 | 69.44 ± 62.14 |

Salmon Calcitonin (sCT)

Oral Delivery

Oral dosing (PO) compositions of delivery agent compound and salmon calcitonin (sCT) in water were prepared. Typically, 450 mg of delivery agent compound was added to 2.0 ml of water. Either the sodium salt of the delivery agent compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (6.5 to 8.5) with NaOH or HCl. 90 µg sCT from a stock solution was added to the solution. Water was then added to bring the total volume to about 3.0 ml (varied depending on the solubility of the delivery agent compound) and vortexed. The final delivery agent compound dose, sCT dose and volume dose amounts are listed below in Table 2.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. The dosing solution was administered by pressing the syringe plunger.

Blood samples were collected serially from the tail artery, typically at time=0, 10, 20, 30, 60 and 90 minutes. Serum sCT levels were determined by testing with an EIA kit (Kit # EIAS-6003 from Peninsula Laboratories, Inc., San Carlos, Calif.). The observed sCT levels were adjusted according to baseline values obtained at time=0. The results from the five rats in each dosing group were averaged for each time point. The maximum is reported below in Table 2.

TABLE 2

Oral Delivery of Salmon Calcitonin (sCT)

| Compound | Volume Dose (ml/kg) | Compound Dose (mg/kg) | sCT Dose (μg/kg) | Mean Peak Serum Sct (pg/ml ± SD) |
|---|---|---|---|---|
| 1 | 1 | 150 | 30 | 164 ± 156 |
| 2 | 1 | 150 | 30 | 112 ± 155 |
| 2 | 1 | 150 | 30 | 482 ± 389 |
| 2 | 1 | 150 | 30 | 206 ± 461 |
| 7 | 1 | 150 | 30 | 206 ± 138 |

Preparation of the Disodium Salt of Compound 1

25 g of the ethanol solvate of compound prepared in Example 1 was dissolved in 250 ml methanol. 5 g of activated carbon was added and the mixture was stirred for 20 minutes at 50–60° C. The slurry was filtered and the carbon treatment was repeated. Methanol was removed in vacuo. The resulting solid was washed with 100 ml of hexane and dried in vacuo. 14.8 g of the disodium salt of compound 1 was recovered as an off-white solid. $^H$NMR indicated that there was no ethanol associated with the purified sample.

The disodium salt of compound 1 was tested in vivo with insulin by the procedure described above for oral administration of insulin. The results are shown below in Table 3.

TABLE 3

Pulmonary Delivery of Insulin with the Disodium Salt of Compound I

| Compound | Volume Dose (ml/kg) | Compound Dose (mg/kg) | Insulin Dose (mg/kg) | Mean Peak Serum Insulin (insulin + Compound) (pg/ml ± SD) (SE) |
|---|---|---|---|---|
| 1 | 0.4 | 0.36 | 0.03 | 166.97 ± 9.64 |
| 1 | 0.4 | 0.18 | 0.03 | 172.10 ± 36.31 |
| 1 | 0.4 | 0.06 | 0.03 | 72.36 ± 29.76 |
| 1 | 0.4 | 0.15 | 0.03 | 35.96 ± 8.5 |
| 1 | 0.4 | 0.03 | 0.03 | 50.66 ± 19.13 |

Heparin Delivery Intracolonic Delivery

Intracolonic (IC) dosing solutions containing a delivery agent compound and heparin sodium USP in 25% aqueous propylene glycol were prepared. Either the sodium salt of the delivery agent compound was used or the free acid was converted to the sodium salt with one equivalent of sodium hydroxide. Typically, the delivery agent compound and heparin (about 166–182 IU/mg) were mixed by vortex as dry powders. This dry mixture was dissolved in 25% v/v aqueous propylene glycol, vortexed and placed in a sonicator (about 37° C.). The pH was adjusted to about 7 (6.5 to 8.5) with aqueous NaOH (2N). The dosing solution was sonicated to produce a clear solution. The final volume was adjusted to 3.0 mL. The final delivery agent compound dose, heparin dose and volume dose amounts are shown in Table 4, below.

The typical dosing and sampling protocols were as follows. Male Sprague-Dawley rats weighing between 275–350 g were fasted for 24 hours and were anesthetized with ketamine hydrochloride (88 mg/kg) intramuscularly immediately prior to dosing. A dosing group of five rats was administered one of the dosing solutions.

For intracolonic (IC) dosing, a 7.5 cm 8 fr Rusch catheter was adapted to a 1 ml syringe with a pipette tip. The dosing catheter was inserted into the colon through the anus until the tube was no longer visible. The dosing solution was expressed slowly into the colon.

Citrated blood samples were collected by cardiac puncture following the administration of ketamine (88 mg/kg), typically at time—0.25, 0.5, 1.0 and 1.5 hours. Heparin activity was determined by utilizing the activated partial thromboplastin time (APTT) according to the method of Henry, J. B., Clinical Diagnosis and Management by Laboratory Methods, Philadelphia, Pa., W. B. Saunders (1979). Previous studied indicated baseline values of about 20 seconds. Results from the five rats in each group were averaged for each time point. The maximum is reported below in Table 4.

TABLE 4

Intracolonic Delivery of Sodium Heparin USP in Rats

| Compound | Volume Dose (ml/kg) | Compound Dose (mg/kg) | Insulin Dose (mg/kg) | Mean Peak Serum Insulin (insulin + Compound) (pg/ml ± SD) |
|---|---|---|---|---|
| 1 | 1 | 750 | 50 | 0 |
| 2 | 1 | 50 | 25 | 74.12 ± 126.28 |
| 2 | 1 | 50 | 25 | 269 ± 42 |
| 3 | 1 | 50 | 25 | 18.3 ± 2.6 |
| 8 | 1 | 20 | 100 | 262.2 ± 182.8 |
| 9 | 1 | 50 | 25 | 68.2 ± 37.1 |

Parathyroid Hormone Delivery (PTH 1–34) Oral/Intracolonic Delivery

Oral gavage (PO) dosing solutions of delivery agent compound and human parathyroid hormone residues 1–34 (PTH) in water were prepared. A solution of the delivery agent compound was made either with the sodium salt of the delivery agent compound or by converting the free acid to its sodium salt. Typically, a solution of the delivery agent compound was prepared in water and stirred, adding one equivalent of sodium hydroxide (1.0 N) when making the sodium salt. The final dosing solutions were prepared by mixing the solution of the delivery agent compound with a PTH stock solution (typically having a concentration of 5 mg PTH/ml) and diluting to the desired volume (usually 3.0 ml). The delivery agent compound, PTH and volume dose amounts are shown in Table 5 below.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. The dosing solution was administered by pressing the syringe plunger.

Blood samples were collected serially from the tail artery, typically at time=0, 15, 30, 45, 60 and 90 minutes for oral dosing. Serum PTH concentrations were quantified by a PTH radioimmunoassay kit (Kit # RIK 6101 from Peninsula Laboratories, Inc. San Carlos, Calif.). Previous studies indicated baseline values of about zero. Results from the five rats in each group were averaged for each time point. The maximum is reported below in Table 5.

TABLE 5

Oral Delivery of PTH in Rats

| Compound | volume dose (ml/kg) | Compound Dose (mg/kg) | PTH Dose (mg/kg) | Mean Peak Serum [PTH] (pg/ml) ± SD |
|---|---|---|---|---|
| 8 | 1 | 100 | 200 | 767.21 ± 140.35 |
| 8 | 1 | 100 | 200 | 276.31 ± 330.06 |
| 8 | 1 | 100 | 200 | 11.31 ± 25.24 |

Interferon—Oral Delivery

Dosing solutions of delivery agent compound and human interferon (IFN) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted to about 7.0 to 8.5. The delivery agent compound solution was mixed with an IFN stock solution (about 22.0 to 27.5 mg/ml in phosphate buffered saline) and diluted to the desired volume (usually 3.0 ml). The final delivery agent compound and IFN doses, and the dose volumes are shown below in Table 6. The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing and again as needed to maintain anesthesia. A dosing group of five rats was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 15, 30, 45, 60 and 90 minutes. Serum IFN concentrations were determined with a Cytoscreen Immunoassay Kit for human IFN-alpha (catalog # KHC4012 from Biosource International, Camarillo, Calif.). Previous studies indicated baseline values of about zero. Results from the rats in each group were averaged for each time point. The maximum of these averages (i.e., the mean peak serum IFN concentration) is reported below in Table 6.

TABLE 6

Interferon - Oral Delivery

| Delivery Agent Compound | Volume dose (ml/kg) | Delivery Agent Compound Dose (mg/kg) | IFN Dose (mg/kg) | Mean Peak Serum [IFN] (ng/ml) ± SD |
|---|---|---|---|---|
| 10 | 1 | 200 | 2 | 0.1256 ± 0.280 |

Recombinant Human Growth Hormone (rhGH) Oral Delivery

Oral gavage (PO) dosing solutions of delivery agent compound and rhGH in phosphate buffer were prepared. A solution of the delivery agent compound was made either with the sodium salt of the compound or by converting the free acid to its sodium salt. Typically, a solution of the delivery agent compound was prepared in phosphate buffer and stirred, adding one equivalent of sodium hydroxide (1.0 N) when making the sodium salt. The final dosing solutions were prepared by mixing the solution containing the deliver agent compound with an rhGH stock solution (15 mg rhGH/ml) and diluting to the desired volume (usually 3.0 ml). The delivery agent compounds and rhGH dose amounts are shown in Table 7 below.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. The dosing solution was administered by pressing the syringe plunger Blood samples were collected serially from the tail artery, typically at time=0, 15, 30, 45, 60 and 90 minutes for oral and 0, 10, 20, 30, 60 and 90 for IC dosing. The five samples from each time period were pooled. Serum rHGH concentrations were determined with an rHGH immunoassay test kit (Kit #K1F4015 from Genzyme Corporation Inc., Cambridge, Mass.). Previous studies indicated baseline values of about zero.

The maximum concentration for each group is reported below in Table 7.

TABLE 7

Oral Delivery of rhGH in Rats

| Compound | Volume dose (ml/kg) | Compound Dose (mg/kg) | rhGH Dose (mg/kg) | Mean Peak Serum (ng/ml) |
|---|---|---|---|---|
| 7 | 1 | 300 | 3 | 49.55 |
| 9 | 1 | 200 | 3 | 0 |

The above-mentioned patents, applications, test methods, and publications are hereby incorporated by reference in their entirety.

Many variations of the present invention will suggest themselves to those skilled in the art in light of the above

What is claimed is:

1. A compound of the formula

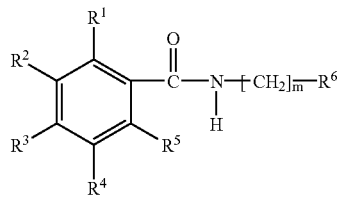

Formula I or a salt thereof, wherein:

R$^1$ is —OH or —OCH$_3$;

R$^2$, R$^3$, R$^4$, R$^5$ are independently selected from hydrogen, halogen, —OH, —OCH$_3$, C$_1$–C$_4$ alkyl, —NH$_2$, —NH(CH$_3$), —N(CH$_3$)$_2$, or —NO$_2$;

m is 0, 1, 3 or 4;

R$^6$ is a phenyl substituted with —O—R$^7$—COOH at the ortho, meta, or para position;

R$^6$ is optionally substituted with one or more members selected from halogen, —OH, —OCH$_3$, C$_1$–C$_4$ alkyl, —NH$_2$, NH(CH$_3$), —N(CH$_3$)$_2$, and —NO$_2$; and R$_7$ is C$_2$–C$_{12}$ n-alkylene, wherein m is 0 when R$^1$ is —OCH$_3$.

2. A compound of the formula

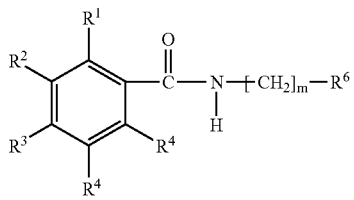

Formulal II or a salt thereof, wherein:

R$^1$ is —OH;

R$^2$, R$^3$, R$^4$, and R$^5$ are independently selected from hydrogen, halogen, —OH, —OCH$_3$, C$_1$–C$_4$ alkyl, —NH$_2$, —NH(CH$_3$), —N(CH$_3$)$_2$, or —NO$_2$;

m is an integer ranging from 0 to 4;

R$^6$ is a phenyl substituted with —O—R$^7$—COOH at the ortho, meta, or para position;

R$^6$ is optionally substituted with one or more members selected from halogen, —OH, —OCH$_3$, C$_1$–C$_4$ alkyl, —NH$_2$, NH(CH$_3$), —N(CH$_3$)$_2$, and —NO$_2$; and R$^7$ is C$_2$–C$_{12}$ n-alkylene.

3. The compound of claim 1 wherein said compound is:

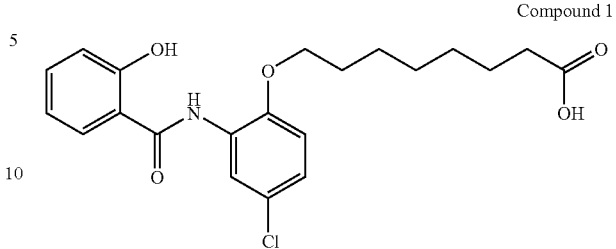

Compound 1 or a salt thereof.

4. The compound of claim 3 wherein said compound is the disodium salt of compound 1.

5. A composition comprising:
(A) an active agent; and
(B) a compound as defined in claim 1.

6. A composition comprising:
(A) an active agent; and
(B) a compound as defined in claim 3.

7. A composition comprising:
(A) an active agent; and
(B) a compound as defined in claim 4.

8. The composition of claim 5, wherein the active agent is selected from the group consisting of a biologically active agent, a chemically active agent, and a combination thereof.

9. The composition of claim 8, wherein the biologically active agent comprises at least one protein, polypeptide, peptide, hormone, polysaccharide, mucopolysaccharide, carbohydrate, or lipid.

10. The composition of claim 9, wherein the biologically active agent is selected from the group consisting of: growth hormones, interferons, interleukin, insulin, heparin, calcitonin, erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, parathyroid hormone, fragments of parathyroid hormone, antimicrobials, anti-fungal agents, vitamins, and analogs, fragments, mimetics and polyethylene glycol (PEG)-modified derivatives of these compounds, and any combination thereof.

11. The composition of claim 10, wherein the biologically active agent comprises insulin, unfractionated heparin, low molecular weight heparin, very low molecular weight heparin, ultra low molecular weight heparin, calcitonin, PTH, EPO, hGH or combinations thereof.

12. The composition of claim 11, wherein the biologically active agent comprises insulin.

13. A dosage unit form comprising:
(A) the composition of claim 5; and
(B) (a) an excipient
  (b) a diluent,
  (c) a disintegrant,
  (d) a lubricant,
  (e) a plasticizer,
  (f) a colorant,
  (g) a dosing vehicle, or
  (h) any combination thereof.

14. The dosage unit form of claim 13, wherein the active agent is selected from the group consisting of a biologically active agent, a chemically active agent, and a combination thereof.

15. The dosage unit form of claim 14, wherein the biologically active agent comprises at least one protein, polypeptide, peptide, hormone, polysaccharide, mucopolysaccharide, carbohydrate, or lipid.

16. The dosage unit form of claim 15, wherein the biologically active agent is selected from the group consisting of: growth hormones, interferons, interleukin, insulin, heparin, calcitonin, erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, parathyroid hormone, fragments of parathyroid hormone, antimicrobials, anti-fungal agents, vitamins, and analogs, fragments, mimetics and polyethylene glycol (PEG)-modified derivatives of these compounds, and any combination thereof.

17. The dosage unit form of claim 15, wherein the biologically active agent comprises insulin, unfractionated heparin, low molecular weight heparin, very low molecular weight heparin, ultra low molecular weight heparin, calcitonin, PTH, EPO, hGH, or combinations thereof.

18. The dosage unit form of claim 17, wherein the active agent comprises insulin.

19. The dosage unit form of claim 13, wherein the dosage unit form is a tablet, a capsule, a powder, or a liquid.

20. The dosage unit form of claim 13, wherein dosing unit form comprises a dosing vehicle and dosing vehicle is selected from the group consisting of water, 25% aqueous propylene glycol, phosphate buffer, 1,2-propane diol, ethanol, and any combination thereof.

21. A method for administering a biologically-active agent to an animal in need of the agent, the method comprising administering to the animal the composition of claim 5.

22. A method for administering a biologically-active agent to an animal in need of the agent, the method comprising administering to the animal via the pulmonary route the composition of claim 7.

23. A method for preparing a composition comprising mixing:
(A) at least one active agent;
(B) the compound of claim 1; and
(C) optionally, a dosing vehicle.

24. The compound of claim 1 wherein said compound is:

Compound 2

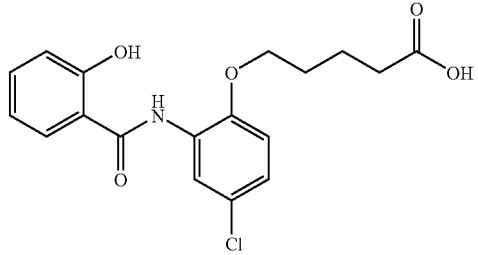

or a salt thereof.

25. The compound of claim 1 wherein said compound is:

Compound 3

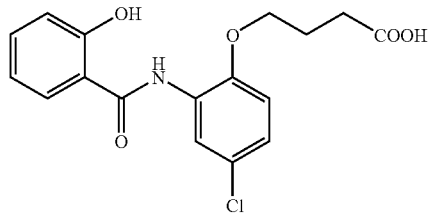

or a salt thereof.

26. The compound of claim 1 wherein said compound is:

Compound 4

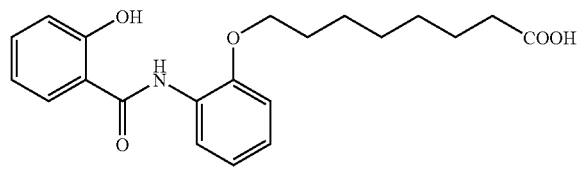

or a salt thereof.

27. The compound of claim 1 wherein said compound is:

Compound 5

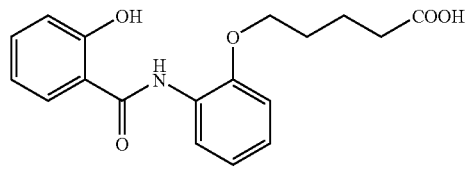

or a salt thereof.

28. The compound of claim 1 wherein said compound is:

Compound 6

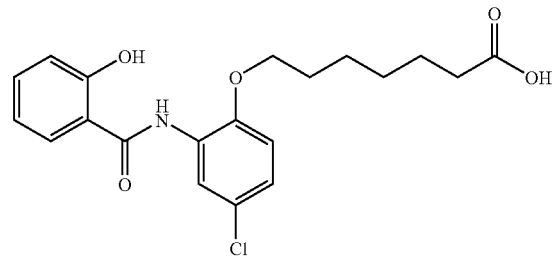

or a salt thereof.

29. The compound of claim 1 wherein said compound is:

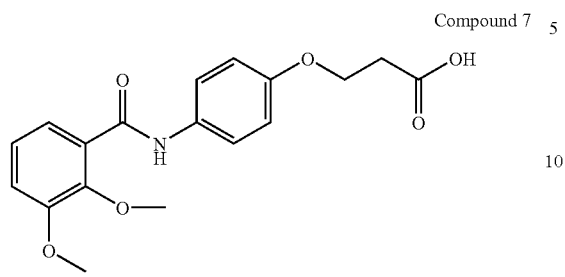
Compound 7

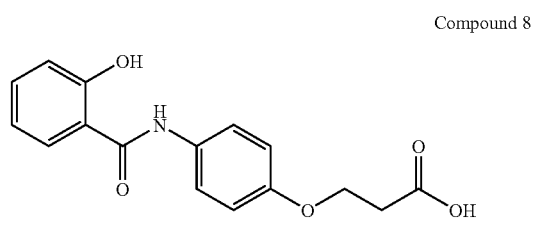
Compound 8

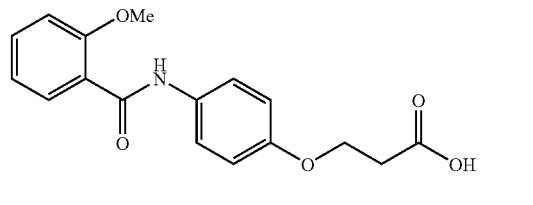
Compound 9

Compound 10
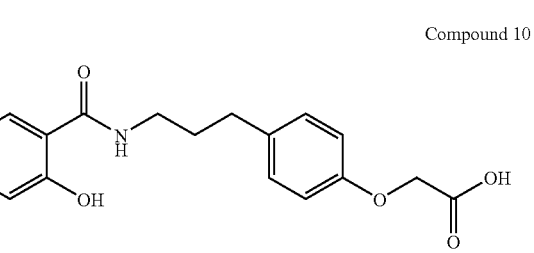

or a salt thereof.

30. The compound of claim 1 wherein said compound is:

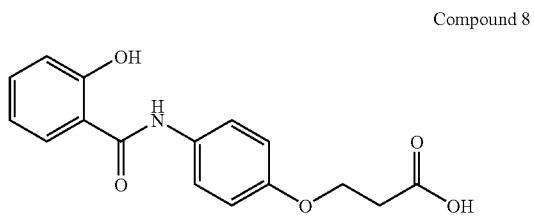
Compound 8 or a salt thereof.

31. The compound of claim 1 wherein said compound is:

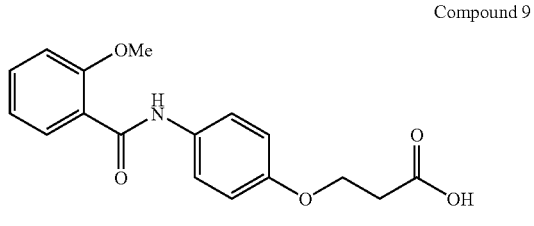
Compound 9 or a salt thereof.

32. A compound of the formula:

Compound 10 or a salt thereof.

33. The compound of claim 1 wherein m is 0.

34. The compound of claim 1, wherein $R^7$ is $C_3$–$C_9$ n-alkylene.

35. The compound of claim 34, wherein $R^7$ is $C_3$–$C_7$ n-alkylene.

36. The compound of claim 1, wherein $R^6$ is substituted with a chlorine at the para position to the O—$R^7$—COOH substituent.

37. The compound of claim 2, wherein m is 1–4.